(12) United States Patent  (10) Patent No.: US 8,224,457 B2
Strandberg et al.  (45) Date of Patent: Jul. 17, 2012

(54) MEDICAL IMPLANTABLE LEAD

(75) Inventors: Hans Strandberg, Sundbyberg (SE); Anna Norlin-Weissenrieder, Stockholm (SE); Leda Henriquez, Bandhagen (SE); Eva Harström, Hässelby (SE); Mikael Sjögren, Fjärdhundra (SE); Annika Naeslund, Bromma (SE); Susanne Nilsson, Huddinge (SE); Olof Stegfeldt, Älta (SE)

(73) Assignee: St. Jude Medical AB, Jarfalla (SE)

( * ) Notice: Subject to any disclaimer, the term of this patent is extended or adjusted under 35 U.S.C. 154(b) by 203 days.

(21) Appl. No.: 12/447,984

(22) PCT Filed: Oct. 31, 2006

(86) PCT No.: PCT/SE2006/001210
§ 371 (c)(1),
(2), (4) Date: Jan. 15, 2010

(87) PCT Pub. No.: WO2008/054259
PCT Pub. Date: May 8, 2008

(65) Prior Publication Data
US 2010/0114279 A1   May 6, 2010

(51) Int. Cl.
*A61N 1/05* (2006.01)

(52) U.S. Cl. ............................................ 607/116

(58) Field of Classification Search ............... 607/118, 607/116
See application file for complete search history.

(56) References Cited

U.S. PATENT DOCUMENTS

| | | | |
|---|---|---|---|
| 5,201,903 A | 4/1993 | Corbett, III et al. | |
| 5,515,848 A | 5/1996 | Corbett, III et al. | |
| 5,964,702 A * | 10/1999 | Grill et al. | 600/377 |
| 6,191,365 B1 | 2/2001 | Avellanet | |
| 6,352,539 B1 | 3/2002 | Avellanet | |
| 6,374,143 B1 * | 4/2002 | Berrang et al. | 607/137 |
| 7,315,761 B2 * | 1/2008 | De Ridder | 607/55 |
| 7,515,968 B2 * | 4/2009 | Metzler et al. | 607/117 |
| 7,697,995 B2 * | 4/2010 | Cross et al. | 607/117 |
| 8,099,172 B2 * | 1/2012 | Swanson | 607/117 |
| 2004/0097965 A1 | 5/2004 | Gardeski et al. | |
| 2006/0089695 A1 | 4/2006 | Bolea et al. | |
| 2006/0217791 A1 | 9/2006 | Spinka et al. | |
| 2009/0099439 A1 * | 4/2009 | Barolat | 600/372 |

* cited by examiner

*Primary Examiner* — Scott Getzow
*Assistant Examiner* — Amanda Patton

(57) ABSTRACT

A medical implantable lead has a proximal end and a distal end, and a flexible flat elongate body. The elongate body includes a layer of strip conductors extending along the length of the flat elongate body, a top insulating layer, and a bottom insulating layer. The layer of strip conductors is sealingly enclosed between the top and bottom insulating layers, and at least a major portion of the flat elongate body is twisted into an elongate helical portion having a central cavity extending longitudinally of the helical portion.

13 Claims, 6 Drawing Sheets

MEDICAL IMPLANTABLE LEAD

BACKGROUND OF THE INVENTION

1. Field of the Invention

The present invention relates to a medical implantable lead having a proximal end and a distal end, and a flat elongate body.

2. Description of the Prior Art

A medical implantable lead is preferably designed as thin as possible. It also needs to be well flexible in order to be able to follow narrow winding body cavities. A conventional structure is an elongate lumen defined, i.e. formed, by coiled conductors carrying electrical signals for different applications. The lumen is used for facilitating implantation of the flexible lead into a body by means of a slightly stiffer guide wire, stylet or the like, which is inserted into the lumen and manoeuvred by an operator, typically a surgeon.

Modern technology imposes demands on increased ability to carry more and more signals for sensing, monitoring and commanding purposes. These demands introduce a conflict between outer diameter of the lead and number of available conductors within the lead, since with the traditional design of the lead a coaxial addition of a conductor coil adds significantly to the diameter of the lead.

Therefore different ways to increase the number of conductors without increasing the outer dimensions of the lead have been proposed. For example, in U.S. Pat. No. 5,201,903 there is shown a multiconductor electrical cable, which is stated to be suitable for implantation in living bodies. The main embodiment has several, e.g. seven, separately insulated conductors, helically twinned to a cable, which is provided with a further insulating coating forming a single, or integral, unit. The conductors are thin wire conductors having diameters as small as about ten micrometers. There is no teaching in this patent as to how to implant such a cable into the body. A central lumen is disclosed, which is meant to be used as a catheter, but being to thin to work as a lumen for a stylet or the like. However, it would probably be a simple task to enlarge the central lumen. Notwithstanding the positive properties of such a thin multi conductor cable, it is also has disadvantages. The manufacturing process of handling such thin wire conductors and embedding them in an insulating material to form the electrical cable is rather a difficult task.

SUMMARY OF THE INVENTION

It is an object of the present invention to provide a medical implantable lead that alleviates the above-mentioned drawbacks of the prior art.

Thus, in accordance with an aspect of the present invention, there is provided a medical implantable lead having a proximal end and a distal end, and comprising a flat elongate body including:
- a layer of strip conductors extending along the length of the flat elongate body;
- a top insulating layer; and
- a bottom insulating layer;
- wherein said layer of strip conductors is sealingly enclosed between said top and bottom insulating layers,
- wherein at least a major portion of said flat elongate body is twisted into an elongate helical portion having a central cavity extending longitudinally of the helical portion.

By making use of modern technology of manufacturing strip conductors it is easy to form a flat elongate body having several conductors, which can be used for any application of interest. However, it is not an easy task to introduce a flat body into a body cavity, since it has different flexibility in different planes in space due to its different width and thickness. This causes difficulties in, for example, forcing the lead into a branching cavity. However, by twisting the flat body into a helical form, it becomes equally flexible in any direction. Furthermore, the cavity that extends longitudinally of the elongate body is usable as a stylet, or guide wire, lumen.

In accordance with an embodiment of the medical implantable lead according to the present invention, the central cavity is a lumen, which is flat in an unused state and expandable in a direction of thickness of the flat elongate body. In this embodiment the lumen is meant to be widened by means of the stylet while the stylet is inserted into the lumen. This facilitates the manufacture of the lead.

In accordance with an embodiment of the medical implantable lead, the central cavity is cylindrical and is defined by a hollow ridge extending along the elongate body on one side of thereof. In other words, looking at a cross-section of the elongate body, the lumen protrudes asymmetrically in one direction from the centre thereof.

In accordance with an embodiment of the medical implantable lead the central cavity is defined by a cylindrical lumen. This is a symmetrical embodiment with a fully centred cavity, which, like the just mentioned embodiment, has it full width from the start.

In accordance with an embodiment of the medical implantable lead, a cross-section of said flat elongate body is arc-shaped. The arc-shape makes the flat body more willing to become twisted.

As defined in accordance with an embodiment of the medical implantable lead, preferably the width of the flat elongate body is less than 3 mm and the thickness thereof is less than 0.3 mm, and even more desirable the width is less than 1 mm and the thickness is less than 0.1 mm.

In accordance with an embodiment of the medical implantable lead, it further comprises a distal end electrode tip, having a number of tip conductors which are connected with the strip conductors of the layer of strip conductors at a distal end of said flat elongate body.

These and other aspects, features, and advantages of the invention will be apparent from and elucidated with reference to the embodiments described hereinafter.

DESCRIPTION OF THE PREFERRED EMBODIMENTS

Figure 1:
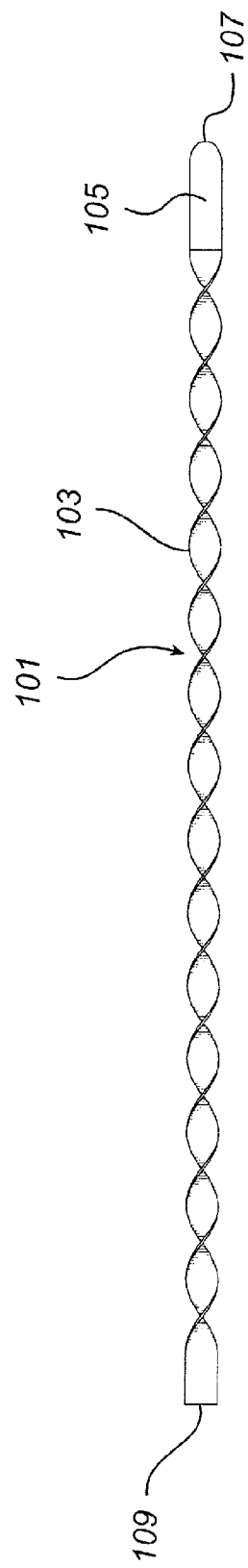
FIG. 1 schematically illustrates an embodiment of a medical implantable lead according to the present invention.
Figure 7:
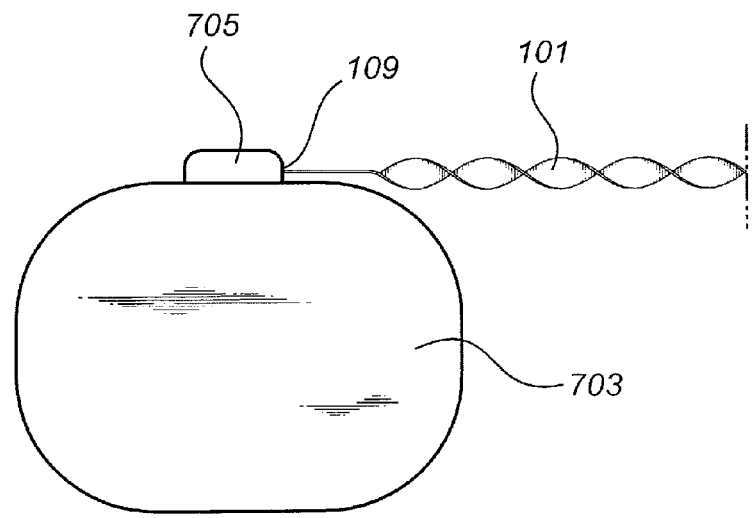
FIG. 7 is a side view illustrating the lead connected to an implantable device.

Referring to FIG. 1, the medical implantable lead 101 generally comprises an elongate body 103, which is basically flat, i.e. ribbon shaped, but a portion thereof has been helically twisted around a longitudinal axis of the elongate body 103. As shown in FIG. 1, typically the portion equals to the whole body 103. In other words, the body turns about its own longitudinal axis. Further, the lead 101 comprises an electrode tip 105 at a distal end 107 thereof. At a proximal end 109 of the lead 101 it is prepared for connection with an implantable device, such as a pacemaker or some other desirable device, see FIG. 7 at 703. The lead 101 comprises plural conductors, as for example exemplified at 203 in FIG. 2, extending between the proximal and distal ends 107, 109.

Figure 2A:
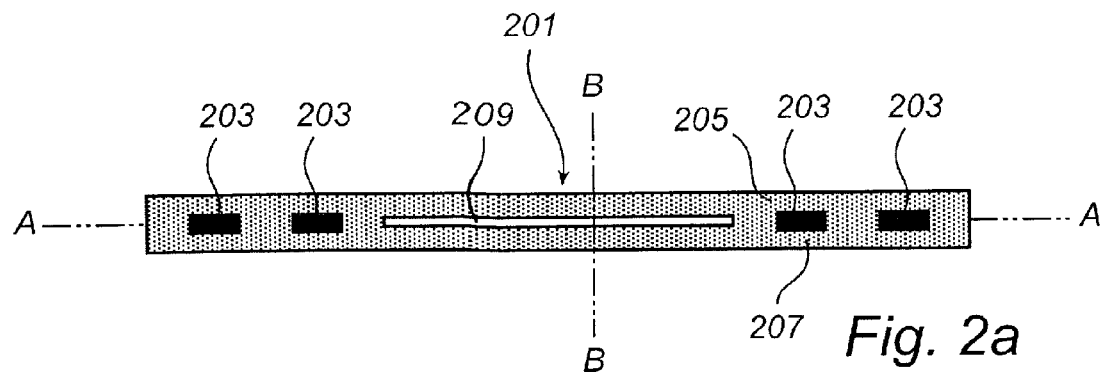
FIGS. 2-4 are schematic cross-sectional views of different embodiments of the medical implantable lead according to the present invention.
Figure 2B:
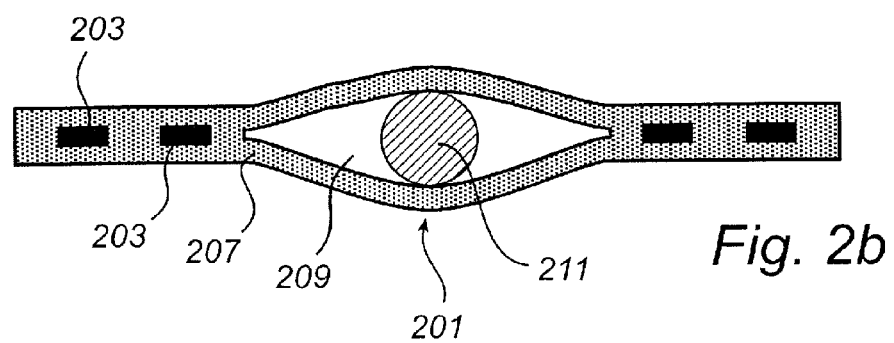

In FIGS. 2a and 2b, a first embodiment of the lead 201 is shown in cross-sectional views taken within the flat elongate and helically twisted body. In FIG. 2a a basic state is shown, and in FIG. 2b an implantation state, is shown. The lead 201 has a layer of strip conductors 203 extending along the length of the flat elongate body, a top insulating layer 205, and a bottom insulating layer 207. The layer of strip conductors 203 is sealingly enclosed between said top and bottom insulating layers 205, 207. A central cavity 209, acting as a lumen for receiving a stylet 211, is formed centrally of the lead 201. The lead 201 is flat in cross-section, i.e. the width is significantly larger than the thickness thereof. In this embodiment, the lumen 209 is substantially closed, or is just a narrow slit, in the basic state, i.e. when no stylet has been introduced into it. When the stylet 211 is being introduced into the lumen 209, it easily widens and provides space for the stylet 211.

Basically, the lead 201 has a lower flexural rigidity in a first plane A containing the longitudinal axis of the lead 201 and extending through the layer of conductors 203, than in a second plane B, also including the longitudinal axis but being orthogonal to the first plane A. However, due to the helical twisting of the lead 201, when an operator is going to implant the lead 201 being in the implantable state, by means of operating the stylet 211, the lead 201 is about equally flexible in all directions, which facilitates the implantation thereof into a body cavity.

It is advantageous to manufacture a flat elongate body, which is then twisted, or manufactured directly into a twisted shape, since it can be manufactured by means of current epitaxial methods, an example of which is to follow. These methods are suitable for manufacturing very small dimension flex cables, and thus, the lead 201 can be made thin and narrow while still including a large number of conductors, which are usable for current supply, control signaling, measurements, etc.

For example the following method of manufacture is applicable. A substrate of an insulating plastic, i.e. the bottom insulating layer 207, is provided. The plastic is chosen from a group of insulating plastics comprising polyimide, polyamide, tetrafluorethene, polyurethane and other biocompatible and biostable plastics. Then the substrate is coated with a metal layer, e.g. cupper or gold. The coating is performed by means of chemical deposition of a thin layer, which is then added onto by more layers until a thickness of about 10 of some tens of micrometers has been obtained. Then a photo resist is applied on top of the metal layer 203. The photo resist is provided with a mask and then hardened. Masked photoresist is then dissolved, by etching, leaving the layer of individual conductors 203, with each conductor 203 having desired predetermined dimensions. Finally an insulating cover, i.e. the top insulating layer 205, is applied. In conjunction therewith the cavity 209 is formed. As is known to anyone familiar with epitaxial manufacturing methods, each step recited above may require several substeps, which will however not be further explained herein, since the invention does not primarily reside in how to manufacture the lead 201.

Figure 3:
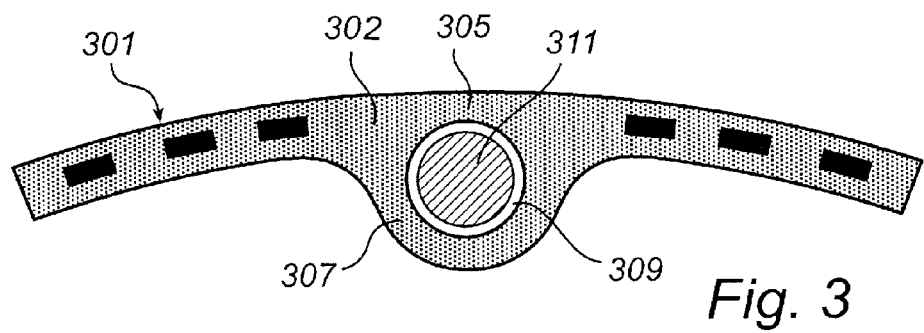

In accordance with a second embodiment of the lead 301, as shown in FIG. 3, the elongate body 302 has the similar structure as that of the first embodiment, except for some differences as follows. The body 302 is arc shaped in a transversal plane. In other words, the body 302 is slightly bent about the longitudinal axis. Thereby it is easier to twist the body 302 about the longitudinal axis thereof. Moreover, the central cavity 309 is preformed in a cylindrical shape. The top insulating layer 305 and the bottom-insulating layer 307, where the bottom-insulating layer forms a longitudinal ridge protruding from the top layer 305, define the cavity. Thus, the cavity 309 can be considered to be off-centered. The inner diameter of the cavity 309 is a bit larger than the outer diameter of a stylet 311 to be inserted into the cavity when the lead 301 is to be implanted.

Figure 4:
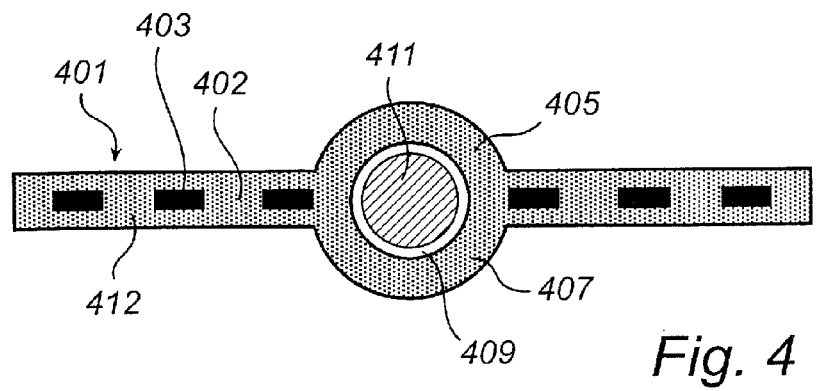

In accordance with a third embodiment of the medical implantable lead 401, as shown in FIG. 4, the elongate body 402 has a similar structure as that of the first embodiment, except for some differences as follows. The central cavity 409 is preformed in a cylindrical shape. The cavity is defined by the top insulating layer 405 and the bottom insulating layer 407 and is fully centered at, i.e. coaxial with, the longitudinal axis of the body 402. The shape of the body 402 can be considered a circular tube, or cylinder, provided with wings, or flanges, 412 extending along opposite sides of the tube, while winding helically around the longitudinal axis thereof. Also in this embodiment the inner diameter of the cavity 409 is a bit larger than the outer diameter of an insertable stylet 411. The conductors are embedded in the wings.

Figure 5A:
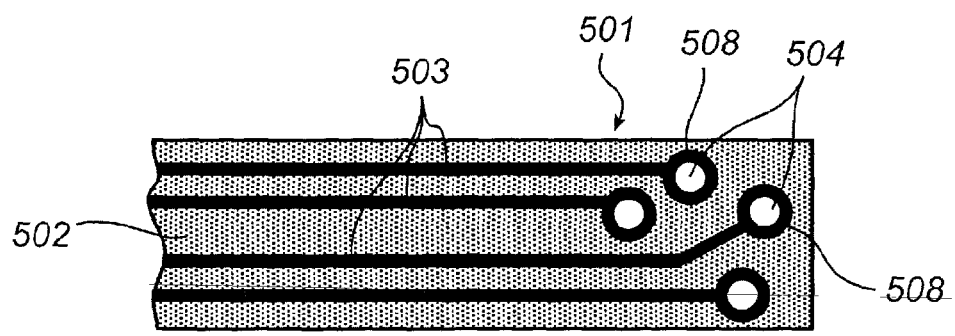
FIGS. 5a-d illustrate a connection process for providing the lead with a electrode tip.
Figure 5B:
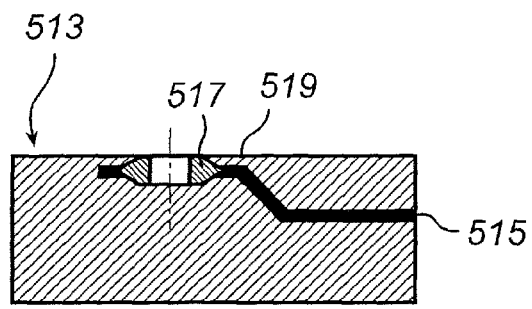
Figure 5C:
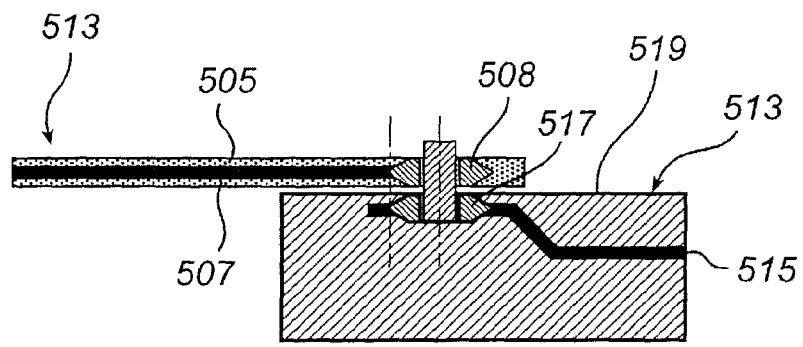
Figure 5D:
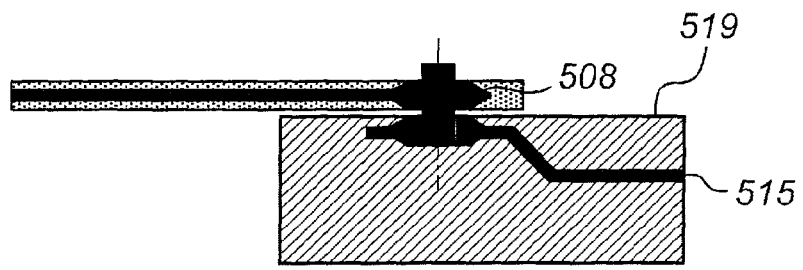
Figure 6:
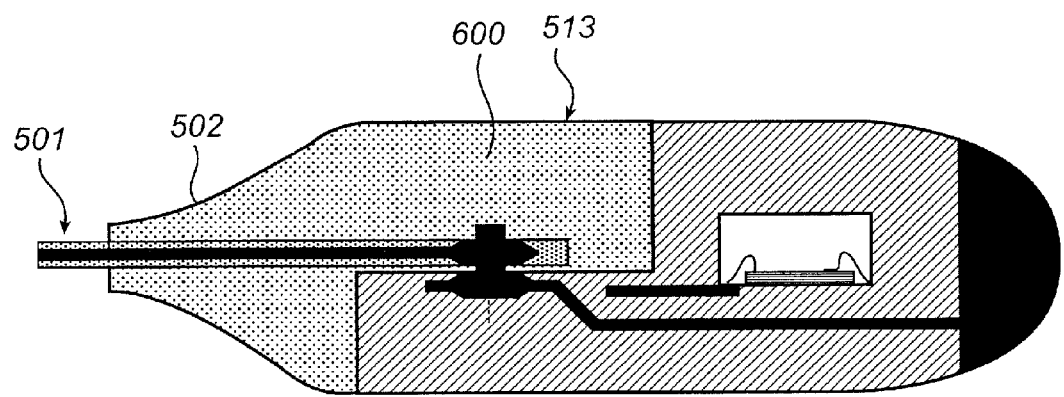
FIG. 6 is a longitudinal section of the electrode tip.

As described above the lead 101 has an electrode tip 105 at the distal end 107 thereof. Referring now to FIGS. 5a-d, at the distal end of the elongate body 502 of the lead 501 the conductors 503 have been made accessible via connection holes 504 extending through the insulating layers and through the ends of the conductors 503. At the end of each conductor there is provided a washer 508, which is connected with the conductor end. The electrode tip 513 is provided with conductors 515, which are also provided with a respective washer 517 at their respective ends at a top surface 519 of the electrode tip 513. The washer 517 of each electrode conductor 515 is accessible through a recess of the top surface 519. The distal end of the elongate body 502 rests on the top surface 519 of the electrode tip 513, such that the washers of the elongate body 502 are aligned with the washers 517 of the electrode tip 513, and a respective connection pin 521 extends through the washers 508, 517 of each pair. This assembly has been welded, such as by laser welding, to form a continuous metallic conductor path. In FIG. 5c the connection is shown before welding and in FIG. 5d it is shown after welding. As shown in FIG. 6, the conductor connection of the conductors 503 of the elongate body 502 and the conductors 515 of the electrode tip 513 is covered by an insulating material 600, which is molded to enclose the connection as well as a portion of the electrode tip 513 and a portion of the elongate body 502 in the vicinity of the connection.

Figure 8A:
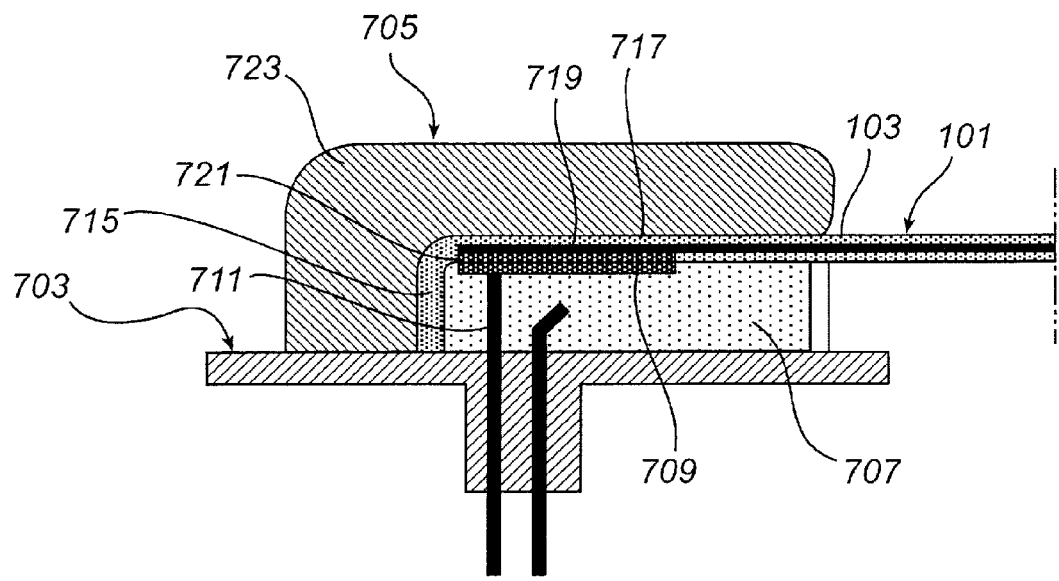
FIGS. 8a-b are sectional views of an interface between the lead and the device shown in FIG. 7.
Figure 8B:
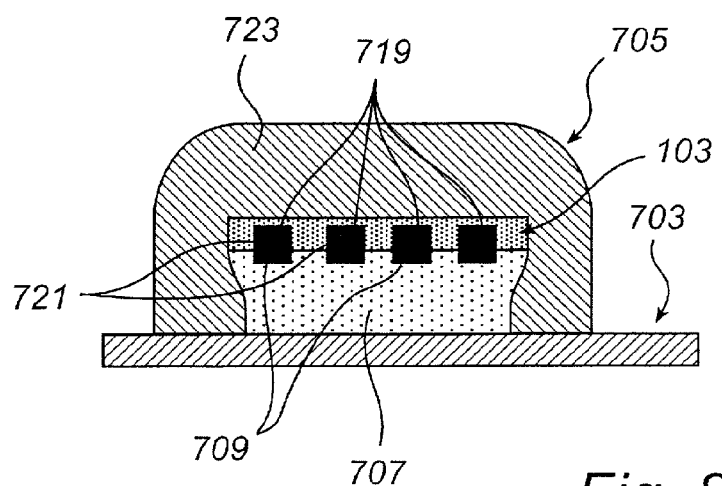

At the proximal end 109 of the lead 101 it is to be connected with an implantable device 703. For that matter a connector 705 has been designed. Referring to FIGS. 8a and 8b, the connector 705 comprises a connector block 707, which is provided with a plurality of strip shaped conductor pads 709, which are arranged on a top surface of the connector block 707. Each conductor pad 709 is connected to a terminal 711 of the device 703 through the connector block 707. The elongate body 103 has a proximal end portion 715 lacking of conductors and being angled perpendicularly to rest of the body 103. The end portion 715 servers as a hook being engaged with an end of the connector block 707, while a contact portion 717, adjacent to said end portion 715, rests on, i.e. is supported by, the top surface of the connector block 707. At a bottom surface of the contact portion 717 it is provided with gold platings 721, one for each conductor 719 of the lead 101. The gold platings are connected with a respective end of the conductors 719 and rest on the corresponding conductor pads 709. The contact portion 717 of the elongate body 103 is held on place and is forced against the conductor pads 709 by means of a connector lid 723, which covers the connector block 707 and connection portion 717. In order to obtain said force the connector block is under-cut along the long side edges thereof. When mounted the connector lid 723 is slided along the connector block 707 from its end at the end portion of the elongate body 103 towards the other end of the connector block 707.

Figure 9:
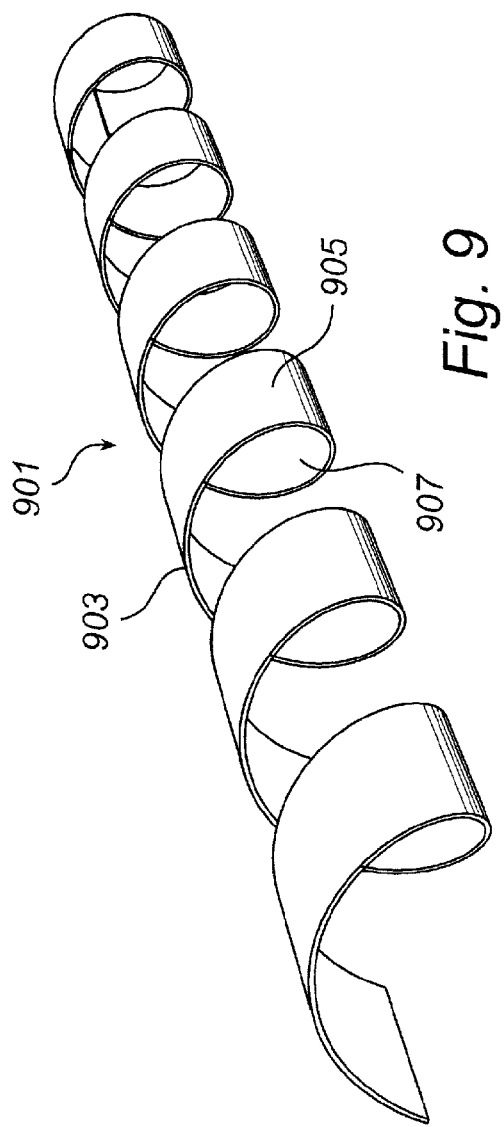
FIGS. 9 and 10 schematically show two further embodiments of a medical implantable lead according to the present invention.
Figure 10:
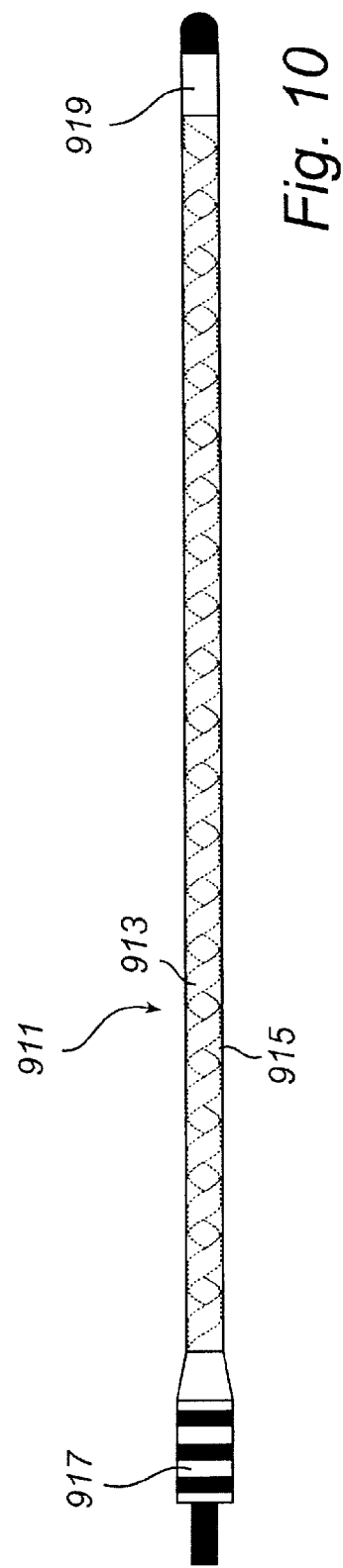

Referring to FIGS. 9 and 10 in a fourth embodiment and a fifth embodiment of the medical implantable lead 901, 911 the twisted elongate body 903, 913 is formed by twisting the original ribbon shaped body into the shape of a helical spring, thus forming a tube, such that one of the top and bottom insulating layers defines the outside 905 of the tube 903, 913 and the other one defines the inside 907 of the tube 903, 913. The tube 903, 913 surrounds a central cavity, which is employed as a stylet lumen. In the fourth embodiment the tube is used as is, while in the fifth embodiment the tube 913, in turn, is enclosed by an outer insulating and liquid sealing tube 915. By connecting a connector 917 to the strip conductors at the proximal end of the elongate body 913, 915 and connecting an electrode tip 919 to the strip conductors at the distal end of the elongate body a lead 911, which both can be operated and looks similar to a conventional lead is accomplished.

Above, embodiments of the medical implantable lead according to the present invention have been described. These should be seen as merely non-limiting examples. As understood by a skilled person, many modifications and alternative embodiments are possible within the scope of the invention as defined by the appended claims.

Although modifications and changes may be suggested by those skilled in the art, it is the intention of the inventors to embody within the patent warranted heron all changes and modifications as reasonably and properly come within the scope of their contribution to the art.

The invention claimed is:

1. A medical implantable lead comprising:
    a flexible, flat elongate body having a longitudinal axis, a proximal end configured for connection to an implantable medical device, a distal end configured for interaction with tissue in vivo, a longitudinal length between said proximal end and said distal end, and a cavity therein extending along the longitudinal length, the cavity adapted to receive a stylet;
    a layer of flat strip conductors extending along said longitudinal length of said flat elongate body;
    a top insulating layer composed of insulating material;
    a bottom insulating layer composed of insulating material;
    said layer of flat strip conductors being sealingly enclosed between said top insulating layer and said bottom insulating layer with insulating material between said flat strip conductors that separates said flat strip conductors in said layer of flat strip conductors from each other in a direction perpendicular to said longitudinal length; and
    at least a substantial portion of said flat elongate body, containing at least a portion of said layer of flat strip conductors, being twisted about said longitudinal axis to form an elongate helical portion.

2. A medical implantable lead as claimed in claim 1 wherein said central cavity forms a lumen that is flat in an unused state and that is expandable in a direction of thickness of said flat elongate body.

3. A medical implantable lead as claimed in claim 1 wherein said central cavity is cylindrical, and is defined by a hollow ridge extending along the elongate body at one side thereof.

4. A medical implantable lead as claimed in claim 1 wherein said central cavity is defined by a cylindrical lumen that is coaxial with a longitudinal axis of said elongate body.

5. A medical implantable lead as claimed in claim 1 comprising an exterior insulating tube that encloses said elongate body.

6. A medical implantable lead as claimed in claim 1 wherein said flat elongate body has an arc-shaped cross-section in a plane traverse the longitudinal axis of the elongate body.

7. A medical implantable lead as claimed in claim 1 wherein said flat elongate body has a width that is less than 3 mm and a thickness that is less than 0.3 mm.

8. A medical implantable lead as claimed in claim 1 wherein said flat elongate body has a width that is less than 1 mm and a thickness that is less than 0.1 mm.

9. A medical implantable lead as claimed in claim 1 comprising an electrode tip at said distal end comprising a plurality of tip conductors respectively connected with said strip conductors.

10. A medical implantable lead as claimed in claim 9 wherein said electrode tip has a top surface on which said elongate body rests, and wherein each strip conductor at said distal end has a washer connected with that strip conductor, and each strip conductor has a washer at said top surface, and wherein the respective washers of the strip conductors are aligned with and connected with the respective washers of the electrode tip by respective connection pins extending through the respective washers.

11. A medical implantable lead as claimed in claim 1 configured to form a pacemaker lead.

12. A medical implantable lead as claimed in claim 1 wherein said strip conductors, at said distal end, are ring-shaped, and comprising connection openings extending through the insulating layers and through the ring-shape of the strip conductors.

13. A medical implantable lead as claimed in claim 1 wherein said top and bottom insulating layers are comprised of plastic, and wherein at least a surface portion of said top insulating layer and said bottom insulating layer is biocompatible.

\* \* \* \* \*